United States Patent [19]

Haberlein et al.

[11] 4,125,501

[45] Nov. 14, 1978

[54] PHOSPHITES OF SUGAR ALCOHOLS AND POLYMERS STABILIZED THEREWITH

[75] Inventors: Harald Häberlein; Norbert Mayer, both of Gersthofen; Gerhard Pfahler, Augsburg, all of Fed. Rep. of Germany

[73] Assignee: Hoechst Aktiengesellschaft, Frankfurt am Main, Fed. Rep. of Germany

[21] Appl. No.: 818,139

[22] Filed: Jul. 22, 1977

[30] Foreign Application Priority Data

Jul. 24, 1976 [DE] Fed. Rep. of Germany ....... 2633392

[51] Int. Cl.$^2$ .......................... C08B 37/00; C08K 5/52
[52] U.S. Cl. .............................. 260/23 H; 260/23 XA; 260/45.8 R; 252/407; 260/45.8 A; 260/45.7 PH; 536/117
[58] Field of Search ..................... 260/45.8 A, 45.8 R, 260/45.7 PH, 45.7 P, 927 R, 982, 937, 928, 30.6, 23 XA, 23 H; 252/403, 403.2, 402.5, 399, 407; 536/117

[56] References Cited

U.S. PATENT DOCUMENTS

| | | | |
|---|---|---|---|
| 2,265,585 | 12/1941 | Urbain et al. | 260/927 R |
| 3,082,189 | 3/1963 | Mack | 536/117 |
| 3,103,507 | 9/1963 | Knoevenagel | 536/117 |
| 3,287,299 | 11/1966 | Cavarius | 260/937 |
| 3,382,236 | 5/1968 | Guttag | 260/982 |
| 3,459,835 | 8/1969 | Dever et al. | 260/927 R |
| 3,472,919 | 10/1969 | Nagy et al. | 536/117 |
| 3,652,743 | 3/1972 | Harris et al. | 260/982 |

*Primary Examiner*—V. P. Hoke
*Attorney, Agent, or Firm*—Connolly and Hutz

[57] ABSTRACT

The present invention relates to novel phosphites of sugar alcohols, their use as stabilizers for organic polymers, to stabilizer compositions containing these novel phosphites and to the organic polymers being stabilized therewith.

The novel phoshites have a good stabilizing effect, especially in combination with known stabilizers, and they are substantially stable to hydrolysis.

6 Claims, No Drawings

PHOSPHITES OF SUGAR ALCOHOLS AND POLYMERS STABILIZED THEREWITH

This invention relates to novel phosphites of polyalcohols stable to hydrolysis, to their manufacture and to their use as stabilizers for synthetic polymers.

In the processing of synthetic polymers in addition to other stabilizers organic phosphites are added to the polymers as costabilizers for quite a long time. Most of the commercial phosphite esters are liquids such as, for example, trisnonylphenyl phosphite, triphenyl phosphite or diphenylisooctyl phosphite. In general, all other stabilizers for plastics materials are solid and, therefore, the addition of the liquid phosphite esters to the pulverulent plastics material necessitate complicate dosing devices. Moreover, liquid additives often detrimentally affect the mechanical properties of the plastics material. The addition of commercial liquid phosphites to rigid PVC reduces, for example, to an undesired extent the so-called Vicat-value, i.e., the temperature at which the plastic starts to become soft. The addition of liquid phosphites to polyolefins may cause the absolutely undesired environmental stress cracking.

These problems have been known for a long time and therefore, it is not surprising that solid phosphites have also been described in literature as stabilizers for plastics, for example esters of long chain alcohols with pentaerythritol, a branched polyol (U.S. Pat. No. 2,961,454). A commercial stabilizer of this group is the distearyl-pentaerythrityl diphosphite, which has the serious drawback to cause discolorations of PVC in processing, so that it has gained a certain importance as polyolefin stabilizer only.

Phosphite esters of anhydro-enneaheptite, a heterocyclic polyol, have also been proposed (cf. U.S. Pat. No. 3,326,939). In practice, however, substances of this type have not yet gained any importance, probably because of the anhydro-enneaheptite not being a commercial product in contradistinction to pentaerythritol and the sugar alcohols.

The hitherto known solid phosphites do have, as generally all organic phosphites, a disadvantageous property which is also latent in liquid phosphites, namely the sensitivity to hydrolysis. With liquid phosphites this property does not matter in view of the fact that they have a small specific surface as a liquid and are generally stored in closed containers impermeable to moisture. For having better dosing properties the solid phosphites must be sold in the form of flowable powders or scales and, therefore, the large specific surface of the fine-grained phosphite considerably facilitates the attack by the omnipresent atmospheric humidity. Moreover, the bag material used for packing the solid phosphite is by far less impermeable than liquid containers and, hence, it is not surprising that on prolonged storage the activity of the usual solid phosphite stabilizers considerably diminishes due to hydrolysis.

It is the object of the present invention to provide solid phosphite stabilizers having an improved stability to hydrolysis for synthetic plastic materials.

It has surprisingly been found that mixed esters of phosphorous acid, linear, open-chain sugar alcohols and long-chain alkyl compounds carrying a functional group with active hydrogen do have the desired properties.

The present invention therefore provides compounds of the formal structure

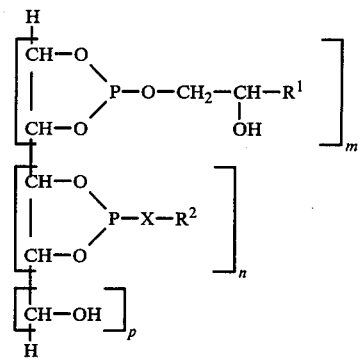

in which
- $m$ is 1 or 2 or 3,
- $n$ is zero or 1 or 2,
- $p$ is zero or 1 or 2, with the proviso that $(2m + 2n + p)$ is equal to or greater than 4 and equal to or smaller than 6,
- $R^1$ represents a linear alkyl radical having from 10 to 30 carbon atoms,
- X represents —O—, —S— or —NR'— with R' being hydrogen or $C_1$ to $C_{20}$ alkyl, and
- $R^2$ represents a linear alkyl radical having from 12 to 30 carbon atoms or a mono- or di-fatty acid ester of the dihydroxypropyl radical, the fatty acid having a chain length of from 12 to 20 carbon atoms.

The invention also provides a process for the manufacture of the aforesaid compounds and their use as stabilizers for plastics materials.

The polyol compounds used to make the compounds of the invention are open-chain sugar alcohols having from 4 to 6 carbon atoms, for example erythritol, adonitol, arabitol, dulcitol, preferably xylitol and especially sorbitol and mannitol.

The phosphorus-containing starting materials are derivatives of phosphorus acid with readily volatile alcohol or amine substituents that can be split off by hydrolysis, for example hexamethyl-phosphorous acid triamide or tri-lower alkyl or triaryl phosphites, for example tripropyl phosphite, triphenyl phosphite and especially trimethyl or triethyl phosphite.

Suitable long-chain alkyl compounds carrying a functional group with active hydrogen are
(a) $\alpha,\beta$-diols of the formula $R^1$ —CH(OH)—$CH_2OH$ having a chain length of from 12 to 32, preferably 20 to 30, carbon atoms, or mixtures of said diols. They can be prepared by hydrolysis in a high yield from the epoxides of long-chain $\alpha$-olefins. The phosphites according to the invention contain at least one radical of such a diol.
(b) Monoalcohols of the formula $R^2$-OH having a chain length of from 12 to 30, preferably 12 to 25, carbon atoms, for example fatty alsohols and wax alcohols, obtained, for example, by hydrogenation of fatty acids and wax acids or contained in natural and fossil waxes or prepared by oligomerization of ethylene, such as synthetic alcohols commercially available by the registered trade mark "Alfol". Preferred alcohols are stearyl and behenyl alcohol. Further preferred alcohol components are glycerol mono- or di-fatty acid esters in which the fatty acid moiety has 12 to 20 carbon atoms, especially glycerol mono- and di-stearate or the commercial mixture of the two substances.

In some cases the compounds defined sub a) and b) are preferably added in a 5 to 15% molar excess.

(c) Aliphatic primary mercaptans of the formula $R^2$-SH having from 12 to 20, preferably 12 to 20, carbon atoms, for example octadecyl mercaptan or dodecyl mercaptan.

(d) Amines of the formula

in which R' represents hydrogen or $C_1$ to $C_{20}$-alkyl and $R^2$ represents $C_{12}$ to $C_{30}$-, preferably $C_{12}$ to $C_{20}$-alkyl, for example lauryl amine, preferably stearyl amine, N-methylstearyl amine and distearyl amine.

Components b), c) and d) can be used in the form of mixtures of the components of the individual groups as well as mixtures of components of several of the groups.

The esters according to the invention are prepared by transesterification from the afore-defined phosphorus containing starting compounds and the substances specified sub a) to d).

The reaction can be accelerated by the addition of basic substances such as alkali metal hydroxide, alkali metal alcoholate, alkali metal amide, alkali metal amine and preferably di- and tri-alkyl amines, for example 2,2,6,6-tetramethyl-4-hydroxypiperidine or triethyl amine. The catalyst is added in an amount of from 0.01 to about 5% by weight, calculated on the total weight of the reaction mixture.

The reaction temperature generally ranges from about 80° to 250° C. In general, the reaction is carried out at a temperature such that the liberated alcohol distils of vividly. It is also possible, of course, and in the case of high boiling alcohols, for example phenol, even advantageous, to promote the separation of the alcohol by pressure reduction. On principle, the reaction could be carried out in the presence of an inert solvent, but, in general, this does not offer any advantage. Owing to the fact that the sugar alcohols have relatively low melting points the reaction takes place in homogeneous phase.

As indicated by the formula, the present invention comprises not only the fully esterified sugar alcohol phosphites but also partially esterified phosphites having up to 2 non-esterified hydroxyl groups; occasionally, the compounds of the latter type being more advantageous.

The term "formal structure" is intended to indicate that the given formula solely defines the gross composition without saying anything about the site of the phosphite ester linkage on the sugar alcohol molecule and the mutual spatial arrangement of the substituents with respect to one another.

The compounds of the invention are readily accessible. They can be prepared, for example, in a single vessel reaction by first charging the reaction vessel with the sugar alcohol, the derivative of phosphorous acid, the long-chain β-hydroxy alcohols and optionally long-chain alcohols, amines or mercaptans in the molar proportion by weight resulting from the formula, optionally adding a basic catalyst and distilling off the substituent of phosphorous acid set free by alcoholysis.

It is likewise possible, of course, to effect the transesterification in stages, i.e., first to react the sugar alcohol and the phosphorous acid ester of a readily volatile alcohol to obtain the corresponding sugar alcohol phosphite ester with short chain alcohol radical and to synthetize the desired compound in the second reaction stage by adding the corresponding molar amount of the long-chain β-hydroxy alcohol and optionally the fatty or wax alcohols, amines or mercaptans and distilling off the liberated amount of readily volatile alcohol. The course of the reaction is illustrated by the following equation. The first reaction stage has been described by O. V. Voskresenskaja, P. A. Kirpienikov and E. T. Mukmenev. Isvest. Akad. Nauk SSSR, Ser.Chim. 1970, 7, 1666–1668).

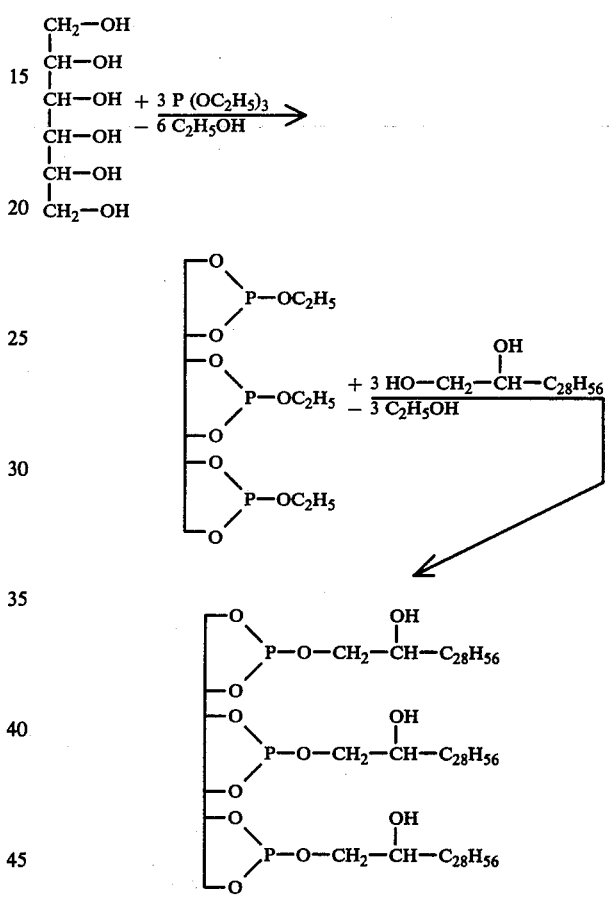

In some cases the single vessel reaction proves to be advantageous, i.e., if the intermediate formed in the two-stage process constitutes a highly viscous, difficultly stirrable mass the manipulation of which is rather cumbersome. With a single vessel process, the formation of a viscous phase is not observed. In the molten state the final products of the reaction represent, in all cases, low viscous liquids which can be filtered and which, after solidification to a waxy mass, can be used without purification. This fact can be considered a special advantage, although it means that the products obtained are not alway chemically uniform compounds and may contain by-products.

A further advantage of the phosphites of the invention is the fact that they are physiologically harmless. The pharmacological test of the acute toxicity in mice showed that the $LD_{50}$ values were above 5,000 mg/kg and even with the highest doses no animal died. According to the classification of W. S. Spector in the "Handbook of toxicology" they can be considered, as far as test results are available, practically non toxic substances. It need not be stressed that the physiological innocuousness of an additive for plastics materials is very important as solely the use of practically non toxic substances can prevent the contamination of foods, coffee, tea, etc. through the packing material.

The sugar alcohol phosphite derivatives of the invention are further characterized by the fact that PVC masses stabilized therewith have an outstanding stability against discoloration under heat.

This fact is surprising and could not have been foreseen for sugar alcohols contain H atoms in $\beta$-position with respect to the oxygen substituents so that under extreme thermal load during processing of the plastics materials so-called $\beta$-elimination reactions with splitting off of phosphorous acid derivatives and formation of conjugated and even cumulated double bonds could have been expected. It is known that highly unsaturated compounds of this type react with one another with the formation of deep brown to black resins. It is really surprising that this phenomenon does not occur, on the contrary the compounds of the invention stabilize PVC very efficiently against discoloration in the so-called "furnace test" for testing the static stability to heat (furnance stability).

Moreover, with the phosphites of the invention the processing stability of moldable compositions, especially on the basis of PVC can be greatly improved. As regards this property, the products are superior to the usual commercial products. This effect, too, is extremely surprising in view of the aforesaid structural and chemical reasons and could not have been foreseen.

It should also be mentioned that the phosphites of the invention have a very high stability to hydrolysis. This is very surprising in that the accumulation of strongly polar groupings in a very narrow section of the molecule, as in the pentite and hexite phosphite esters, would rather suggest a high sensitivity to hydrolysis.

The sugar alcohol phosphite esters of the invention are also very efficient in the stabilization of polyolefins. The addition of usual amount thereof (less than 1% by weight) to polypropylene considerably improves the stability to light and to heat, especially in the presence of phenolic and optionally sulfidic antioxidants.

Phenolic and sulfidic stabilizers are intended to include the heat stabilizers generally used in plastics processing, for example 3,5-di-tert.butyl-4-hydroxyphenyl-propionic acid esters, 2,6-ditert.-butyl-p-cresol, alkylidene-bis-alkylphenols, esters and salts of bis(4'-hydroxy-3'-tert.butylphenyl)-butanonic acid or of cycloalkylidene-(bis-alkylphenol)-carboxylic acids as well as thiodipropionic acid esters of fatty alcohols or dioctadecyl sulfide and disulfide.

The phosphites of the invention are used as stabilizers in an amount of from 0.05 to 5 parts by weight, preferably 0.1 to 3 parts by weight for 100 parts by weight of polymer to be stabilized.

A stabilizer combination having a synergistic effect in the processing of halogen-free poly-$\alpha$-olefins, for example high, medium and lower pressure homopolymers of $C_2$ to $C_4$-$\alpha$-olefins, especially polyethylene and polypropylene, or of copolymers of such $\alpha$-olefins, consists, for example, of 0.05 to 3 parts by weight of a phenolic stabilizer, 0.05 to 2 parts by weight of the calcium salt of a fatty acid or a wax acid (such as stearic acid or montanic acid), optionally 0.1 to 3 parts by weight of a sulfidic stabilizer and 0.05 to 5, preferably 0.1 to 3, parts by weight of one or several of the sugar alcohol phosphite derivatives of the invention, for 100 parts by weight of polymer. If necessary, 0.01 to 3 parts by weight of a special UV stabilizer can be added to the mixture. From among the great number of commercial UV stabilizers the following are named by way of example: alkoxyhydroxy-benzophenones, hydroxyphenyl-benztriazoles, salicylic acid phenyl esters, benzoic acid hydroxyphenyl esters, benzylidene-malonic acid mononitrile esters and so-called quenchers such as nickel chelates, hexamethylphosphoric acid triamide or piperidine stabilizers known as "HALS" products (hindered amine light stabilizers).

An addition of the phosphite compounds of the invention, besides metal compounds known as stabilizers, epoxide stabilizers and optionally polyhydric alcohols, improves the heat and light stability not only in polyvinyl chloride processing but generally of chlorine-containing polymers such as chloropolyethylene or chlorine-containing vinyl homo- and copolymers, for example polyvinylidene chloride, polyvinyl chloroacetate and vinyl chloride-$\alpha$-olefin copolymers.

Metal compounds known as stabilizers in this context are calcium, barium, strontium, zinc, cadmium, magnesium, aluminum and lead soaps of aliphatic carboxylic acids or hydroxycarboxylic acids having approximately 8 to 32 carbon atoms, preferably 8 to 20 carbon atoms, or of phenol-substituted aliphatic carboxylic acids, salts of the said metals with aromatic carboxylic acids preferably having 7 to 12 carbon atoms, for example benzoates, salicylates and (alkyl)-phenolates with alkyl radicals having from 1 to 12, preferably 1 to 6, carbon atoms. Further compounds of this type are organo-tin compounds, for example dialkyl-tin thioglycolates and carboxylates and optionally neutral and basic lead salts of inorganic acids such as sulfuric acid and phosphoric acid.

Known epoxide stabilizers are, for example, epoxidized higher fatty acids such as epoxidized soybean oil, tall oil or linseed oil, and epoxidized butyl oleate and the epoxides of long-chain $\alpha$-olefins.

Suitable polyhydric alcohols are, for example, pentaerythritol, trimethylol propane, sorbitol, or mannitol, i.e., preferably alcohols having 5 or 6 carbon atoms and 3 to 6 hydroxyl groups.

A suitable stabilizer combination for the processing of halogen-containing polymers, for example chlorinated polyolefins or chlorine-containing vinyl homo- and copolymers, consists, for example, of 0.05 to 5 parts by weight of one or several of the phosphite compounds of the invention, 0.1 to 10 parts by weight of metal compounds known as stabilizers, 0.1 to 10 parts by weight of a known epoxide stabilizer and 0 to 1 part by weight of a polyhydric alcohol, for 100 parts by weight of polymer.

Mixtures of phosphite esters of sugar alcohol of the invention with known stabilizers improve not only the stability of polyolefins and chlorinated polymers but also of polyesters, polyamides, phenol-formaldehyde resins, epoxide resins, polystyrene, polyacrylonitrile, polycarbonates, polysiloxanes, polyethers, polyurethanes and SBR rubber mixtures.

The following examples illustrate the invention.

EXAMPLE 1

Tri-(β-hydroxy-triacontyl)-sorbityl-triphosphite

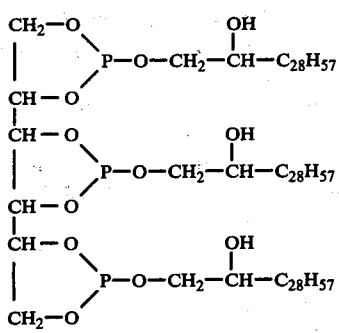

While passing through dry nitrogen, a mixture of
- 18.2 g (0.1 mol) of sorbitol,
- b 51 g (0.3 mol) of triethyl phosphite,
- 150 g (0.3 mol) of a $C_{30}$-1,2-diol, prepared by hydrolysis of a $C_{30}$-epoxide obtained under the conditions of Examples 9 to 12 of British Pat. No. 1,452,730, and
- 1 ml of triethyl amine was stirred at a bath temperature of about 120° C. in a 500 ml three-necked flask provided with stirrer, gas-inlet, 10 cm Vigreux column and distillation bridge. After about 1 hour, ethanol started to distil over. Thereafter, the bath temperature was adjusted in a manner such that the outlet temperature of the distillation bridge did not exceed the boiling temperature of ethanol (78° C.). About 50 ml of ethanol distilled over. Towards the end of the reaction the bath temperature was increased to about 200° C.

When the development of ethanol had ceased, unreacted triethyl phosphite was removed by applying a water jet vacuum for a short period of time. The molten product was filtered through a heated folded filter and allowed to cool.

A waxy product melting at 81° C. was obtained in an almost quantitative yield.

EXAMPLE 2

Di-(β-hydroxy-triacontyl)-sorbityl-diphosphite

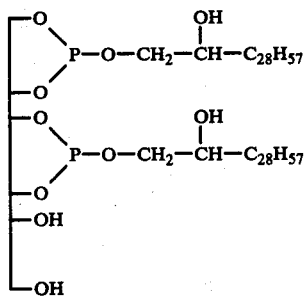

Under the conditions of Example 1 a product melting at 78°–80° C. was prepared from sorbitol, triethyl phosphite and $C_{30}$-1,2-diol in a molar proportion of 1:2:2 in the presence of catalytic amounts of triethyl amine, while distilling off the split off ethanol.

EXAMPLE 3

Di-(β-hydroxy-triacontyl)-mannityl-diphosphite

This compound was prepared under the conditions of Example 2, using mannitol instead of sorbitol. The substance melted at 75°–79° C.

EXAMPLE 4

Di-(β-hydroxy-triacontyl)-mono-thiododecyl-sorbityl-triphosphite

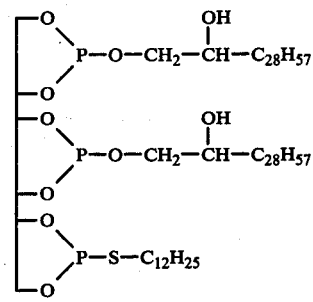

The compound was prepared under the condition of Example 1 by heating a mixture of sorbitol, triethyl phosphite, $C_{30}$-1,2-diol and n-dodecyl-mercaptan in a molar proportion of 1:3:2:1 in the presence of a small amount of triethyl amine, while distilling off the liberated ethanol. The product melted at 72°–74° C.

EXAMPLE 5

Di-(β-hydroxy-eicosyl)-mono-thiododecyl-mannityl-triphosphite

The compound was prepared as described in Example 4 with the use of mannitol. It melted at 75°–80° C.

EXAMPLES 6 to 9

Sorbitol-tris-phosphites of the formula

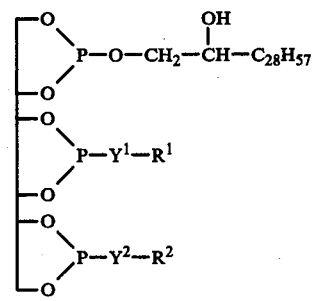

were prepared as described in Example 1. In the following table the reaction components used and the melting points of the products obtained are listed.

| Example No. | $R^1$—$Y^1$—H | $R^2$—$Y^2$—H | m.p. ° C |
|---|---|---|---|
| 6 | stearyl alcohol | stearyl alcohol | 73–75 |
| 7 | glycerol monostearate* | glycerol monostearate | 73–79 |
| 8 | stearyl amine | stearyl amine | 96–104 |
| 9 | stearyl alcohol | distearyl amine | 68–71 |

*industrial grade glycerol monostearate, i.e. a mixture of about 55 % of glycerol monostearate, about 35 % of glycerol distearate and about 10 % of glycerol tristearate.

EXAMPLE 10

To test the acute toxicities of the compounds of the invention male albino mice were fed as prescribed in the book "Grundlagen der experimentellen Arzneimittelforschung" by Leopold Ther, addition 1965.

The phosphite to be tested was administered per os, suspended in aqueous methyl cellulose (Tylose$^R$) solution, to groups of 5 test animals each, the doses being 1,000, 2,000, and 5,000 mg/kg of body weight.

As phosphite the di-($\beta$-hydroxy-triacontyl)-sorbityl-diphosphite of Example 2 was tested. Even with the highest dosage no animal died, so that the compound can be considered practically innocuous.

EXAMPLE 11

This example is intended to demonstrate the surprisingly high stability to hydrolysis of the phosphites of the invention as compared with phosphites of the state of the art.

The stability to hydrolysis was tested according to the process disclosed in DT-OS 2,144,181, pages 7/8. 5.0 g each of the respective phosphite were boiled for 20 and 60 minutes in 100 ml of deionized water. The mixture was then allowed to cool, it was filtered to remove residues, if any, and in the filtrate the liberated phosphorous acid was titrated with 0.1N KOH against bromophenol blue.

In the following table is indicated the degree of hydrolysis determined under the specified conditions as quotient of the actual consumption of KOH and the theoretically possible consumption with a complete hydrolysis.

| phosphite of Example | degree of hydrolysis after | |
|---|---|---|
| | 20 minutes | 60 minutes |
| | in % of theory | |
| 1 | 1.8 | 2.4 |
| 2 | 22.5 | — |
| 3 | 21.0 | — |
| 4 | 1.5 | 3.6 |
| 5 | 1.0 | 2.0 |
| 6 | 9 | — |
| comparative phosphites | | |
| distearyl-pentaerythrityl-diphosphite | 55 | 68 |
| triphenyl phosphite | 84 | 100 |
| trisnonylphenyl phosphite | 57 | 92 |
| di-phenyl-isooctyl-phosphite | 55 | 72 |

EXAMPLE 12

This example is intended to demonstrate the stabilizing effect of the phosphites of the invention in polyvinyl chloride. The parts in the following description are parts by weight.

Each time 100 parts of a mass polyvinyl chloride having a K value of 60 were intimately mixed with
- 0.2 part of 2-phenyl-indole,
- 3.0 parts of epoxidized soybean oil
- 0.25 part of a complex calcium/zinc stabilizer consisting of 42% by weight of calcium stearate, 30% by weight of zinc stearate, 22% weight of pentaerythritol and 6% by weight of 2,6-di-tert.butyl-4-methylphenol
- 0.2 part of a montanic acid ester (acid number 18, esterification number 154)
- 0.3 part of stearyl stearate
- 0.5 part of glycerol monostearate and
- 0.5 part each of respective phosphite of the invention.

To measure the dynamic heat stability (rolling stability) the mixtures were rolled on a two roll mill at 180° C. and with 20 revolutions per minute. At intervals of 10 minutes samples were taken from the rough sheet and the color of the samples was compared with the colors of a proper color chart. Rolling was continued until the rough sheet had turned black.

In order to measure the staic heat stability (furnace stability) a rough sheet was prepared as described above by rolling the mixture for 10 minutes at 180° C. on a two roll mill. Flat samples having a diameter of about 30 mm were punched out of the rough sheet removed from the mill and having a thickness of about 0.5 mm, the samples were wrapped in aluminum foil and heated to 180° C. in a heating cabinet with air circulation. At intervals of 10 minutes each a sample was taken from the cabinet and the color thereof was compared with that of the color chart. In the following table the time is indicated until the sample had turned black.

In the color chart used the individual notes have the following meaning:
1 = water clear
2 = slightly yellowish
3 = intense yellow color
4 = dark yellow-brown color
5 = dark brown to black It can be seen from the following table that the phosphites of the invention give excellent results as regards the dynamic as well as the static stabilization effect and that they are distinctly superior to commercial phosphites.

| phosphite of Example | stabilization effect of the phosphites of the invention in PVC dynamic (rolling) stability discoloration of rough sheet after a rolling time of | | | | | | | | static (furnace) stability black coloration at 180° C after |
|---|---|---|---|---|---|---|---|---|---|
| | 10' | 20' | 30' | 40' | 50' | 60' | 70' | 80' | |
| 1 | 1 | 1–2 | 2 | 2–3 | 3 | 3 | 4 | 4 | 60' |
| 2 | 1 | 1–2 | 2 | 2–3 | 3 | 4 | 5 | — | 60' |
| 3 | 1 | 1–2 | 2 | 2–3 | 3 | 4 | 5 | — | 60' |
| 4 | 1 | 2 | 2 | 3 | 3 | 4 | 5 | — | 60' |
| 5 | 1 | 2 | 2–3 | 3 | 3 | 4 | 5 | — | 60' |
| 6 | 1 | 1–2 | 2 | 2–3 | 3 | 3–4 | 4 | 4–5 | 60' |
| 7 | 1 | 1–2 | 2 | 2–3 | 3 | 3 | 4 | 5 | 60' |
| comparison | | | | | | | | | |
| distearyl-pentaerythrityl diphosphite | 2–3 | 2–3 | 3 | 4 | 5 | — | — | — | 50' |
| triphenyl phosphite | 1 | 2 | 2–3 | 5 | — | — | — | — | 50' |
| trisnonylphenyl phosphite | 1 | 2 | 2–3 | 3 | 5 | — | — | — | 40' |
| diphenyl-isooctyl phosphite | 1 | 2–3 | 3 | 5 | — | — | — | — | 70' |

EXAMPLE 13

This example is intended to demonstrate the stabilizing effect of the phosphites of the invention in polypropylene.

A mixture of
100 parts of unstabilized pulverulent polypropylene having a density of 0.90 (melt index $i_5$ about 6 g/10 min, determined analogous to ASTM D 1238-62 T)
0.15 part of laurin-thiodipropionic acid ester
0.10 part of bis(4'-hydroxy-3'-tert.butylphenyl)-butanoic acid ester and
0.20 part of a phosphite of the invention was homogenized for 5 minutes at 200° C. on a two roll mill.

The molten composition was then molded at 200° C. into a sheet 1 mm thick and from the cold sheet test specimens according to DIN 53,455 were cut out.

To determine the stability to light the test specimens were exposed to the changing light of a Xenotest apparatus, type 150, by Messrs. Hanau Quarzlampen GMBH, the irradiation intensity being modulated by 6 IR filters and 1 UV window (DIN 53,387). The time of exposure in hours was measured after which the absolute elongation at break had dropped to 10% of the initial value. The elongation at break was measured in the Instron tensile testing machine at a draw off speed of 5 cm/min. The energy of radiation absorbed per square centimeter was calculated from the time of exposure and the intensity of irradiation.

The test results are listed in the following table.

Effectiveness of the phosphites of the invention in polypropylene

| phosphite of Example | exposure time in hours | radiation energy (KJ/cm$^2$) |
|---|---|---|
| 1 | 578 | 12.6 |
| 6 | 672 | 14.7 |
| 7 | 642 | 14.2 |
|  | 195 | 4.7 |

It can be seen that the phosphites of the invention are excellently suitable for stabilizing polyolefins.

What is claimed is:

1. A compound of the formula I

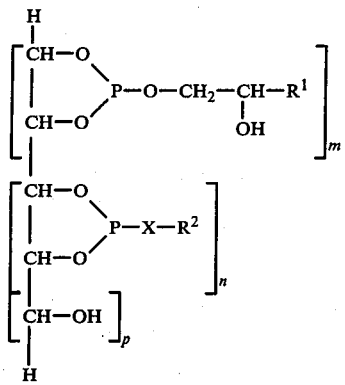

in which
m is 1 or 2 or 3,
n is zero or 1 or 2,
p is zero or 1 or 2, with the proviso that (2m + 2n + p) is equal to or greater than 4 and equal to or smaller than 6,
R$^1$ represents a linear alkyl radical having from 10 to 30 carbon atoms,
X represents —O—, —S— or —NR'— with R' being hydrogen or C$_1$ to C$_{20}$ alkyl, and
R$^2$ represents a linear alkyl radical having from 12 to 30 carbon atoms.

2. A compound as claimed in claim 1, wherein (2m + 2n + p) is 6, X represent oxygen and R$^2$ stands for a linear alkyl radical having from 12 to 20 carbon atoms.

3. Process for stabilizing homopolymers and copolymers of halogen-free, C$_2$ to C$_4$-α-olefins, chlorinated polyolefins and chlorine-containing vinyl homo- and copolymers against the detrimental effect of light and heat, which comprises adding to the said polymers during processing from 0.05 to 5.0 parts by weight, for 100 parts by weight of polymer, of at least one compound as claimed in claim 1.

4. Moldable plastics composition consisting essentially of a member selected from the group of homopolymers and copolymers of halogen-free C$_2$ to C$_4$ alpha-olefins, chlorinated polyolefins and chlorine-containing vinyl homo- and copolymers and containing as stabilizer a compound as claimed in claim 1 in an amount of from 0.05 to 5.0 parts by weight per 100 parts by weight of polymer.

5. Stabilizer combination for homopolymers and copolymers of halogen-free C$_2$ to C$_4$-α-olefins, consisting of 0.05 to 5.0 parts by weight of at least one compound as claimed in claim 1, 0.05 to 3.0 parts by weight of a known phenolic stabilizer, 0.05 to 2.0 parts by weight of a calcium salt of a fatty acid or a wax acid, 0 to 3.0 parts by weight of a known sulfidic stabilizer and 0 to 3.0 parts by weight of a known UV stabilizer.

6. Stabilizer combination for chlorinated polyolefins and chlorine-containing vinyl homo- and copolymers, consisting of 0.05 to 5.0 parts by weight of at least one compound as claimed in claim 1, 0.1 to 5.0 parts by weight of a metal soap known as stabilizer, 0.1 to 5.0 parts by weight of a known epoxide stabilizer and 0 to 1.0 part by weight of a polyhydric alcohol.

* * * * *